(12) United States Patent
Shen et al.

(10) Patent No.: US 10,345,247 B2
(45) Date of Patent: Jul. 9, 2019

(54) APPARATUS FOR DETECTING DEGREE OF PARTICULATE CONTAMINATION ON FLAT PANEL

(71) Applicant: SHANGHAI MICRO ELECTRONICS EQUIPMENT (GROUP) CO., LTD., Shanghai (CN)

(72) Inventors: Yongqiang Shen, Shanghai (CN); Xiaoqing Yang, Shanghai (CN); Xueshan Han, Shanghai (CN)

(73) Assignee: SHANGHAI MICRO ELECTRONICS EQUIPMENT (GROUP) CO., LTD., Shanghai (CN)

( * ) Notice: Subject to any disclaimer, the term of this patent is extended or adjusted under 35 U.S.C. 154(b) by 0 days.

(21) Appl. No.: 15/907,736

(22) Filed: Feb. 28, 2018

(65) Prior Publication Data
US 2018/0246040 A1 Aug. 30, 2018

(30) Foreign Application Priority Data
Feb. 28, 2017 (CN) .......................... 2017 1 0114472

(51) Int. Cl.
*G01N 21/88* (2006.01)
*G01N 21/94* (2006.01)
(Continued)

(52) U.S. Cl.
CPC ......... *G01N 21/8806* (2013.01); *G01N 21/94* (2013.01); *G01N 21/95* (2013.01);
(Continued)

(58) Field of Classification Search
CPC .. G01N 21/8806; G01N 21/892; G01N 21/94; G01N 21/95; G01N 21/9501;
(Continued)

(56) References Cited

U.S. PATENT DOCUMENTS

| | | | | |
|---|---|---|---|---|
| 4,391,524 A | * | 7/1983 | Steigmeier | G01N 21/9501 356/237.1 |
| 4,464,050 A | * | 8/1984 | Kato | G11B 7/00375 250/559.45 |
| 4,598,997 A | * | 7/1986 | Steigmeier | G01N 21/94 250/559.41 |
| 4,794,264 A | * | 12/1988 | Quackenbos | G01N 21/88 250/559.16 |
| 4,794,265 A | * | 12/1988 | Quackenbos | G01N 21/88 250/559.45 |

(Continued)

FOREIGN PATENT DOCUMENTS

JP 07297248 A * 11/1995

*Primary Examiner* — Gordon J Stock, Jr.
(74) *Attorney, Agent, or Firm* — Muncy, Geissler, Olds & Lowe, P.C.

(57) ABSTRACT

An apparatus for detecting a degree of particulate contamination on a flat panel is disclosed, including: an illuminator for producing a radiation beam which results in scattered radiation from its scattering by contaminants on a surface of the flat panel under test and reflected radiation from its reflection by the surface of the flat panel under test; a detector for collecting the scattered radiation, the detector having a radiation collection surface perpendicular to a normal of the surface of the flat panel under test; and a beam trimmer for separating the reflected radiation from the scattered radiation, the beam trimmer including a first optical member, disposed in correspondence with the scattered radiation and configured for directing the scattered radiation to be collected by the detector, and a second optical member disposed in correspondence with the reflected radiation and configured for directing the reflected radiation not to be collected by the detector.

11 Claims, 5 Drawing Sheets

(51) Int. Cl.
  *G01N 21/95* (2006.01)
  *G01N 21/956* (2006.01)
(52) U.S. Cl.
  CPC . *G01N 21/9501* (2013.01); *G01N 2021/9513* (2013.01); *G01N 2021/95676* (2013.01); *G01N 2201/0638* (2013.01)
(58) Field of Classification Search
  CPC ....... G01N 21/9506; G01N 2021/9511; G01N 2021/9513; G01N 2201/0638; G01N 2201/068
  USPC ......... 356/237.1–237.6, 238.3, 239.1–239.3, 356/239.7, 239.8
  See application file for complete search history.

(56) References Cited

U.S. PATENT DOCUMENTS

| | | | |
|---|---|---|---|
| 2001/0048761 A1* | 12/2001 | Hamamatsu | G01N 21/8851 382/149 |
| 2002/0122174 A1* | 9/2002 | Hamamatsu | G01N 21/9501 356/237.2 |
| 2007/0229833 A1* | 10/2007 | Rosencwaig | G01B 11/303 356/426 |
| 2008/0174771 A1* | 7/2008 | Yan | G01N 21/8901 356/237.5 |
| 2011/0019197 A1* | 1/2011 | Meeks | G01N 21/474 356/446 |
| 2016/0293052 A1* | 10/2016 | Sapora | G09B 23/00 |

* cited by examiner

APPARATUS FOR DETECTING DEGREE OF PARTICULATE CONTAMINATION ON FLAT PANEL

CROSS-REFERENCES TO RELATED APPLICATIONS

This application claims the priority of Chinese patent application number 201710114472.3, filed on Feb. 28, 2017, the entire contents of which are incorporated herein by reference.

TECHNICAL FIELD

The present invention relates to the field of semiconductor technology and, in particular, to an apparatus for detecting a degree of particulate contamination on a flat panel.

BACKGROUND

Contamination control is crucial to the yield of a semiconductor integrated circuit (IC) or flat panel display fabrication process. Detection of contamination (including foreign particles, fingerprints, scratches, pinholes, etc.) is necessary prior to the exposure of a mask, wafer or glass substrate.

Apparatuses for the detection of particulate contamination in the existing photolithography tools usually utilize a dark-field scattering technique as explained in FIG. 1, in which a radiation beam 11 emanated from a radiation source 10 is scattered on contaminants on a mask 40 carried on a mask stage 30, and scattered radiation therefrom is collected by a detector 20 as a test signal. However, such a detection apparatus is susceptible to crosstalk from mirrored particles (particularly in case of a chrome bottom surface of the mask) as well as crosstalk from a pattern on the mask bottom surface (as shown in FIGS. 2 and 3 which illustrate experimentally captured original images), which may significantly degrade the signal-to-noise ratio (SNR) of the test signal and hence the detection accuracy. For example, particles present on the chrome bottom surface of the mask in which the pattern to be exposed is formed will be mirrored by the chrome surface into virtual images called mirrored particles which can undesirably cross talk with the test signal.

In order to overcome this issue, a solution has been proposed in which a theoretical configuration as shown in FIG. 4 is determined based on an analysis on the impact of crosstalk from the pattern and mirrored particles on an angle of incidence 50, an angle of collection 60 and an illumination field of view (FoV). However, in this solution, the configuration fails to take into account all possible angles of incidence 50 and collection 60. When the angle of collection 60 is very close to the angle of reflection, as shown in FIG. 5, the reflected radiation 13 will overlap an edge of an FoV of the imaging module 20 and intensify the scattered radiation 12 to be collected, leading to inaccurate determination. Additionally, in this solution, an optical axis of the imaging module 20 must be aligned with the angle of collection 60 which, however, is subject to constraints from other system parameters. Therefore, the supporting, assembly and clamping of the imaging module 20 must be adjusted whenever there is a change in the angle of collection 60. Thus, the compatibility of this solution is inferior.

SUMMARY OF THE INVENTION

In order to overcome the above-described problems, the present invention provides an apparatus for detecting a degree of particulate contamination on a flat panel.

To this end, the present invention provides an apparatus for detecting a degree of particulate contamination on a flat panel, including: an illuminator configured for producing a radiation beam, wherein the radiation beam is scattered by contaminants on a surface of a flat panel under test and results in a scattered radiation, and the radiation beam is reflected by the surface of the flat panel under test and results in a reflected radiation; a detector configured for collecting the scattered radiation, the detector having a radiation collection surface perpendicular to a normal of the surface of the flat panel under test; and a beam trimmer configured for separating the reflected radiation from the scattered radiation, the beam trimmer including a first optical member and a second optical member, the first optical member disposed in correspondence with the scattered radiation and configured for directing the scattered radiation to be collected by the detector, the second optical member disposed in correspondence with the reflected radiation and configured for directing the reflected radiation away from the detector.

Preferably, the scattered radiation is directed to be incident at right angles on the radiation collection surface of the detector and is thereby collected by the detector.

Preferably, the beam trimmer may include a reflecting prism with an outer surface of the reflecting prism defining a first radiation-transmitting area, a second radiation-transmitting area and an outer radiation-reflecting area, the first radiation-transmitting area, the second radiation-transmitting area and an inner radiation-reflecting area of the reflecting prism together constituting the first optical member, the first radiation-transmitting area facing toward the scattered radiation, the second radiation-transmitting area facing toward the detector, the reflecting prism configured for directing the scattered radiation to pass through the first radiation-transmitting area onto the inner radiation-reflecting area and further directed by the inner radiation-reflecting area to pass through the second radiation-transmitting area onto the detector, the outer radiation-reflecting area on the outer surface of the reflecting prism corresponding to the reflected radiation and constituting the second optical member, the reflected radiation being incident on and reflected by the outer radiation-reflecting area so as not to be received by the detector.

Preferably, the reflecting prism may have a cross-section in a shape of a trapezoid with a top surface, a bottom surface, a first slanted side and a second slanted side; the top surface and the bottom surface are parallel to the surface of the flat panel under test; the bottom surface is closer to the detector with respect to the top surface; the first slanted side defines the first radiation-transmitting area corresponding to the scattered radiation; the bottom surface defines the second radiation-transmitting area; and the scattered radiation enters the reflecting prism through the first slanted side and is first incident onto and reflected by an inner surface of the second slanted side of the reflecting prism and then incident onto and reflected by an inner surface of the first slanted side so that the scattered radiation exits the reflecting prism through the bottom surface and is finally collected by the detector.

Preferably, the first slanted side may be perpendicular to an optical axis of the scattered radiation, and when defining an angle between the first slanted side and the bottom surface as a first angle $\theta 1$, an angle between the bottom surface and the second slanted side as a second angle $\theta 2$, an angle between the second slanted side and the top surface as a third angle $\theta 3$ and an angle between the top surface and the first slanted side as a fourth angle $\theta 4$, the first to fourth angles, as well as a diameter l of the first radiation-transmitting area on the first slanted side of the reflecting prism, satisfy:

$$\theta1=90°-(90°-theta1);$$

$$\theta2=180°-1.5\times theta1;$$

$$\theta3=1.5\times theta1;$$

$$\theta4=180°-theta1; \text{ and}$$

$$l=2\times d1\times\tan(alpha1)$$

where, theta1 denotes an angle between the optical axis of the scattered radiation and the normal of the surface of the flat panel under test, alpha1 represents an object-side angle of view of the scattered radiation with respect to the reflecting prism, and d1 denotes a distance from a center of an illumination field of view created by the illuminator on the surface of the flat panel under test to the first slanted side of the reflecting prism.

Preferably, the first optical member may include a first reflector and a second reflector; the second optical member may include a third reflector; the first reflector faces toward the scattered radiation; the scattered radiation is sequentially reflected by the first reflector and the second reflector and is thereby incident on the detector; the third reflector faces toward the reflected radiation; and the reflected radiation is reflected by the third reflector so that the reflected radiation is not collected by the detector.

Preferably, an angle θ5 between the first reflector and the flat panel under test may satisfy θ5=180°−1.5×theta1; the second reflector is disposed on a same line as the third reflector and is closer to the flat panel under test with respect to the third reflector; the second reflector and the third reflector are both oriented at an angle θ6 with respect to the flat panel under test, which satisfies θ6=180°−theta1; and a lengthwise dimension of the first reflector is greater than 2×d1×tan(alpha1), a lengthwise dimension of the second reflector is greater than 2×(d1+d3)×tan(alpha1) and a lengthwise dimension of the third reflector is greater than 0 and smaller than 2×(h1−h2), where theta1 denotes an angle between the optical axis of the scattered radiation and the normal of the surface of the flat panel under test; alpha1 denotes an object-side angle of view of the scattered radiation with respect to the first reflector; d1 denotes a distance from a center of the illumination field of view created by the illuminator on the surface of the flat panel under test to an optical axis of the second reflector extending along a propagation direction of the scattered radiation; h1 denotes a distance from a location of the third reflector stricken by the reflected radiation to the flat panel under test, which satisfies h1=d2/tan(beta); h2 denotes a distance from a highest intersection point between the scattered radiation and a line that is perpendicular to the flat panel under test and passes the location of the third reflector stricken by the reflected radiation to the flat panel under test, which satisfies h2=d2/tan(theta1−alpha1); and beta denotes an angle between the normal of the surface of the flat panel under test and the radiation beam.

Preferably, the illumination field of view created by the illuminator may be a linear illumination field of view.

Preferably, the detector may include an imaging optical path and a time-delay integration camera, and wherein after being separated from the reflected radiation by the beam trimmer, the scattered radiation is converged onto the time-delay integration camera via the imaging optical path.

Preferably, the reflecting prism may have a cross-section in the shape of a right trapezoid.

Compared with the prior art, the apparatus of the present invention includes: an illuminator configured for producing a radiation beam, wherein the radiation beam is scattered by contaminants on a surface of a flat panel under test and results in a scattered radiation, and the radiation beam is reflected by the surface of the flat panel under test and results in a reflected radiation; a detector configured for collecting the scattered radiation, the detector having a radiation collection surface perpendicular to a normal of the surface of the flat panel under test; and a beam trimmer configured for separating the reflected radiation from the scattered radiation, the beam trimmer including a first optical member and a second optical member, the first optical member disposed in correspondence with the scattered radiation and configured for directing the scattered radiation to be collected by the detector, the second optical member disposed in correspondence with the reflected radiation and configured for directing the reflected radiation away from the detector. Compared with conventional apparatuses, the present invention adds the beam trimmer between the illuminator and the detector to separate the scattered radiation from the reflected radiation so as to ensure the reflected radiation not to reach the detector. In addition, configuring the radiation collection surface of the detector 200 perpendicular to the normal to the surface of the flat panel under test 400 on which the radiation beam 101 produced by the illuminator 100 can improve the adaptability to different system configurations.

BRIEF DESCRIPTION OF DRAWINGS

In FIGS. 1 to 5: 10—radiation source; 11—radiation beam; 12—radiation taken as a test signal; 13—reflected radiation; 20—detector; 30—mask stage; 40—mask; 50—angle of incidence; and 60—angle of collection.

In FIGS. 6 to 9: 100—illuminator; 101—radiation beam; 102—scattered radiation; 103—reflected radiation; 200—detector; 300—panel stage; 400—flat panel under test; 500—angle of incidence; 600—angle of collection; 700— radiation-reflecting area; 800, 900—radiation-transmitting areas; 70—first reflector; 90—second reflector; and 80—third reflector.

DETAILED DESCRIPTION OF EXEMPLARY EMBODIMENTS

Specific embodiments of the present invention are described below in greater detail so that its foregoing objectives, features and advantages will become more apparent and readily understandable. It is to be noted that the drawings are presented in a very simplified form not necessarily presented to scale, with the only intention to facilitate convenience and clarity in explaining the embodiments.

Embodiment 1

Figure 6:
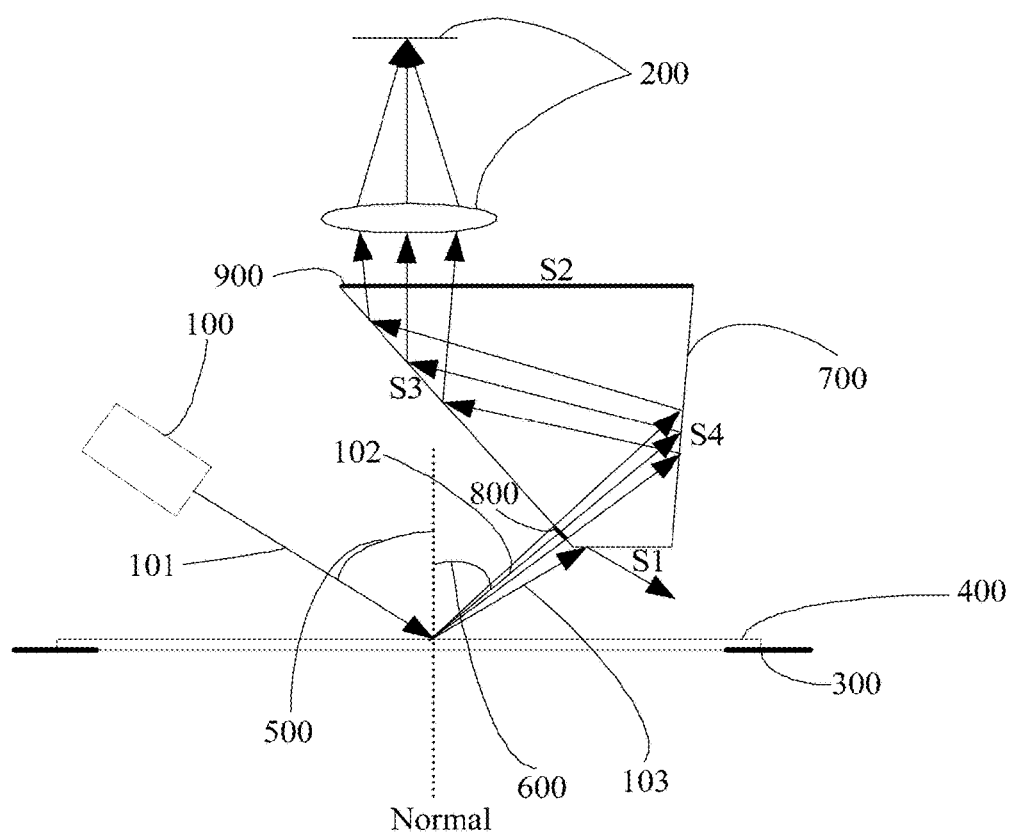
FIG. 6 is a structural schematic of an apparatus for detecting a degree of particulate contamination on a flat panel according to a first embodiment of the present invention.

The present invention provides an apparatus for detecting a degree of particulate contamination on a flat panel, as shown in FIG. 6, including:

an illuminator 100 configured to create an illumination field of view (FoV) which may be a linear FoV.

a detector 200 configured to collect scattered radiation from a radiation beam 101 that is produced by the illuminator 100 and scattered on contaminants on the surface of the flat panel under test 400 carried on a panel stage 300, the detector 200 having a radiation collection surface perpendicular to a normal to the surface of the flat panel under test 400 on which the radiation beam 101 produced by the illuminator 100 is incident;

a beam trimmer configured to separate the scattered radiation 102 from reflected radiation 103 resulting from the radiation beam striking the top surface of the flat panel under test 400. Specifically, the detector 200 may include an imaging optical path and a time-delay integration (TDI) camera, and after separation from the reflected radiation 103, the scattered radiation 102 may be converged to the TDI camera via the imaging optical path.

In this embodiment, the beam trimmer is implemented as a reflecting prism. The surface areas (including outer surface areas and inner surface areas) of the reflecting prism are divided into radiation-transmitting areas 800, 900 and radiation-reflecting areas 700. The scattered radiation 102 enters the reflecting prism through the radiation-transmitting area 800, and then it is reflected by the inner surfaces of the reflecting prism and exits the reflecting prism from the radiation-transmitting area 900 and finally arrives at the detector 200. The reflected radiation 103 is reflected by the radiation-reflecting area 700 so that it is not collected by the detector 200. In this way, the reflected radiation 103 is separated from the scattered radiation 102, and it is ensured that the reflected radiation 103 does not reach the detector 200. Thus, the reflected radiation 103 will not affect the detection accuracy.

Figure 7:
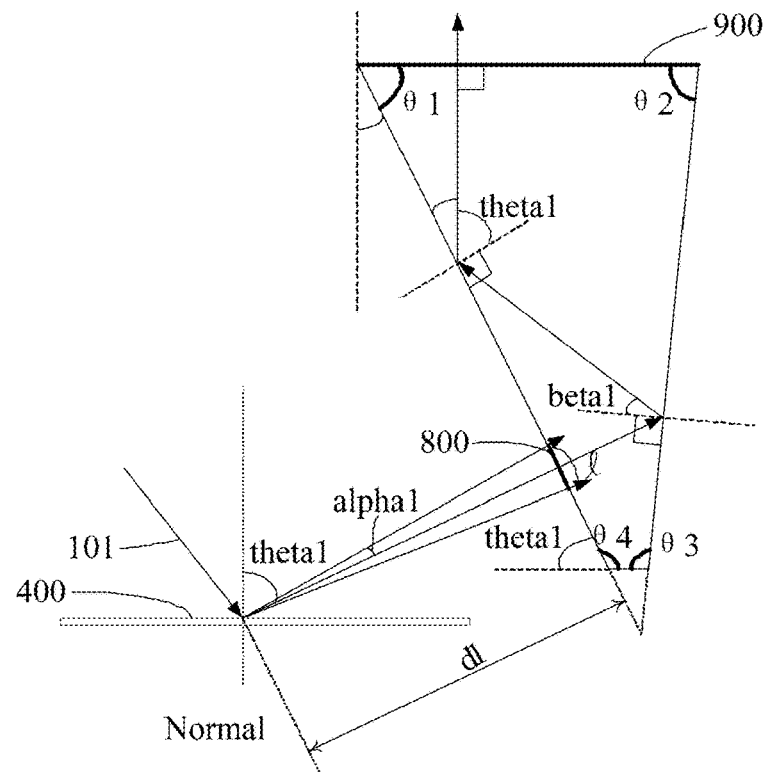
FIG. 7 schematically shows configuration parameters of the apparatus according to the first embodiment of the present invention.

Preferably, referring to FIGS. 6 and 7 with emphasis, the reflecting prism has a cross-section in the shape of a trapezoid, preferably a right trapezoid. In the context of this embodiment, description is made with the cross-section of the reflecting prism not being in the shape of a right trapezoid as an example. The reflecting prism has a top surface S1 (the lower surface as per the illustrated orientation) and a bottom surface S2 (the upper surface as per the illustrated orientation) both parallel to the surface of the flat panel under test 400. The reflecting prism further has a first slanted side S3 (the left side as per the illustrated orientation), on which the radiation-transmitting area 800 is defined, and a second slanted side S4 (the right side as per the illustrated orientation). After entering the reflecting prism through the radiation-transmitting area 800, the scattered radiation 102 is first incident on the inner surface of the first slanted side S3 and then reflected onto the second slanted side S4; after being further reflected by the second slanted side S4, the scattered radiation 102 exits the reflecting prism from the bottom surface S2 through the radiation-transmitting area 900 and is finally collected by the detector 200. In this embodiment, the reflected radiation 103 is externally reflected at the top surface S1 so that it does not enter into the reflecting prism and is not collected by the detector 200. Specifically, of the reflecting prism, the angle between the bottom surface S2 and the first slanted side S3 is defined as a first angle $\theta 1$, the clockwise next angle, i.e., the angle between the bottom surface S2 and the second slanted side S4, as a second angle $\theta 2$, the clockwise third angle, i.e., the angle between the second slanted side S4 and the top surface S1, as a third angle $\theta 3$, and the clockwise fourth angle, i.e., the angle between the top surface S1 and the first slanted side S3, as a fourth angle $\theta 4$. The first to fourth angles, as well as a size (e.g. diameter)/of the radiation-transmitting area 800 on the first slanted side S3, satisfy:

$$\theta 1 = 90° - (90° - \text{theta1});$$

$$\theta 2 = 360° - 90° - 2 \times \text{theta1} - (90° - \text{beta1}) = 180° - 1.5 \times \text{theta1};$$

$$\theta 3 = 180° - 2\theta 2 = 1.5 \times \text{theta1};$$

$$\theta 4 = 180° - \text{theta1}; \text{ and}$$

$$l = 2 \times d1 \times \tan(\text{alpha1})$$

where, theta1 denotes an angle between the scattered radiation 102 and the normal; alpha1, an object-side angle of view of the scattered radiation 102 with respect to the reflecting prism; d1, the distance from a center of the illumination FoV to the first slanted side S3 of the reflecting prism; and beta1, an angle of reflection of the scattered radiation 102 at the second slanted side S4 of the reflecting prism.

Because the first slanted side S3 of the reflecting prism is oriented at an angle of (90°−theta1) with respect to the normal, and since 2×beta1=90°−theta1, it can be derived that beta1=theta1÷2.

Assuming alpha1=0.8°, theta1=60° and d1=10 mm, from the above equations, we can get:

$\theta 1 = 60°$, $\theta 4 = 120°$, $\theta 2 = 90°$, $\theta 3 = 90°$ and $l = 0.28$ mm.

A design of the reflecting prism based on these data allows the detector 200 to always maintain its orientation. In addition, using reflecting prisms of different designs enables a single detector 200 to collection radiation of all angles of scattering 600.

For instance, in order to detect contaminant stripes on the surface of the flat panel under test 400 resembling a one-dimensional grating with a period ranging from 70 μm to 150 μm and a duty cycle of 0.8, a 630-nm radiation source may be used, with an angle of incidence 500 of 62°, theta1=60° and alpha1=0.8°. Based on the grating equation d[sin(theta_i)−sin(theta_m)]=mλ (where, d denotes the period of the grating; theta_i, the angle of incidence; theta_m, angle of the m-th order scattering; and λ, the incident wavelength), rigorous coupled wave analysis (RCWA) simulations may be performed to compute angles and efficiencies of scattering at different orders (the zero-th order corresponds to the reflected radiation).

TABLE 1

Grating Scattering Angles

| Period (μm) | Order | | | | |
|---|---|---|---|---|---|
| | 0 | 1 | 2 | 3 | 4 |
| | Angle of Scattering (°) | | | | |
| 70 | 62 | 60.92067 | 59.87672 | 58.86458 | 57.88121 |
| 75 | 62 | 60.99148 | 60.01400 | 59.06462 | 58.14078 |
| 80 | 62 | 61.05357 | 60.13460 | 59.24061 | 58.36947 |
| 85 | 62 | 61.10845 | 60.24137 | 59.39665 | 58.57249 |
| 90 | 62 | 61.15732 | 60.33657 | 59.53597 | 58.75395 |
| 95 | 62 | 61.20111 | 60.42199 | 59.66111 | 58.91711 |
| 100 | 62 | 61.24057 | 60.49906 | 59.77413 | 59.06462 |
| 105 | 62 | 61.27632 | 60.56894 | 59.87672 | 59.19862 |
| 110 | 62 | 61.30885 | 60.63261 | 59.97026 | 59.32091 |
| 115 | 62 | 61.33858 | 60.69085 | 60.05590 | 59.43294 |
| 120 | 62 | 61.36586 | 60.74432 | 60.13460 | 59.53597 |
| 125 | 62 | 61.39098 | 60.79360 | 60.20716 | 59.63103 |
| 130 | 62 | 61.41418 | 60.83916 | 60.27429 | 59.71902 |
| 135 | 62 | 61.43568 | 60.88140 | 60.33657 | 59.80070 |
| 140 | 62 | 61.45566 | 60.92067 | 60.39451 | 59.87672 |
| 145 | 62 | 61.47427 | 60.95727 | 60.44854 | 59.94766 |
| 150 | 62 | 61.49165 | 60.99148 | 60.49906 | 60.01400 |

TABLE 2

Grating Scattering Efficiencies

| Period (μm) | Order | | | | |
|---|---|---|---|---|---|
| | 0 | 1 | 2 | 3 | 4 |
| | Scattering Efficiency (°) | | | | |
| 70 | 59.5354676% | 2.4919393% | 1.6600029% | 0.7564912% | 0.1707591% |
| 75 | 59.5366043% | 2.4914145% | 1.6579864% | 0.7545835% | 0.1699296% |
| 80 | 59.5371385% | 2.4909737% | 1.6561859% | 0.7528666% | 0.1691802% |
| 85 | 59.5379850% | 2.4905857% | 1.6546352% | 0.7513923% | 0.1685384% |
| 90 | 59.5383877% | 2.4901931% | 1.6531978% | 0.7500445% | 0.1679588% |
| 95 | 59.5390425% | 2.4898891% | 1.6519621% | 0.7488676% | 0.1674469% |
| 100 | 59.5392678% | 2.4895500% | 1.6508047% | 0.7477952% | 0.1669907% |
| 105 | 59.5395965% | 2.4892861% | 1.6497851% | 0.7468318% | 0.1665749% |
| 110 | 59.5398727% | 2.4890013% | 1.6488379% | 0.7459583% | 0.1662053% |
| 115 | 59.5400487% | 2.4887630% | 1.6479739% | 0.7451502% | 0.1658598% |
| 120 | 59.5402981% | 2.4885231% | 1.6471881% | 0.7444278% | 0.1655551% |
| 125 | 59.5403440% | 2.4882997% | 1.6464498% | 0.7437481% | 0.1652685% |
| 130 | 59.5405231% | 2.4880960% | 1.6457829% | 0.7431352% | 0.1650104% |
| 135 | 59.5405562% | 2.4878881% | 1.6451441% | 0.7425552% | 0.1647687% |
| 140 | 59.5406694% | 2.4877137% | 1.6445695% | 0.7420267% | 0.1645462% |
| 145 | 59.5406905% | 2.4875206% | 1.6440161% | 0.7415313% | 0.1643423% |
| 150 | 59.5407309% | 2.4873573% | 1.6435093% | 0.7410704% | 0.1641502% |

The collected scattered radiation 102 is as presented in the following table.

TABLE 3

Collected Scattered Radiation

| Period (um) | Order | Scattering Efficiency |
|---|---|---|
| 70 | 2 | 1.6600029% |
| 75 | 2 | 1.6579864% |
| 80 | 2 | 1.6561859% |
| 85 | 2 | 1.6546352% |
| 90 | 2 | 1.6531978% |
| 95 | 2 | 1.6519621% |
| 100 | 2 | 1.6508047% |
| 105 | 2 | 1.6497851% |
| 110 | 2 | 1.6488379% |
| 115 | 2 | 1.6479739% |
| 120 | 2 | 1.6471881% |
| 125 | 2 | 1.6464498% |
| 130 | 3 | 0.7431352% |
| 135 | 3 | 0.7425552% |
| 140 | 3 | 0.7420267% |
| 145 | 3 | 0.7415313% |
| 150 | 3 | 0.7410704% |

If the scattered radiation 102 is greater than or equal to 10 times the noise of the detector, it can be effectively detected. Therefore, the detector is required to have an SNR of at least $10 \times 1.6600029\% \div 0.7410704\% = 22.4$.

If the angle of collection theta1 changes to 61.2° due to system assembly errors or other reasons, for grating-like contaminant stripes of any size, the first-order scattered radiation may be collected as the test signal. However, in case of the arrangement of FIG. 4, at least part of the reflected radiation (i.e., the radiation of the zero-th order) will be incident on an edge portion of the imaging module, as shown in FIG. 5. In this case, the detector is required to have an SNR of at least $10 \times 59.5407309\% \div 2.4873573\% = 239.8$. As no existing detectors have an SNR greater than 150, the detection could not be successfully achieved.

In contrast, with the arrangement according to the present invention using the reflecting prism with the aforementioned design parameters, the reflected radiation 103 (i.e., the radiation of the zero-th order) will be reflected away at the edge of the radiation-transmitting area 800 of the reflecting prism. As such, the separation of the scattered radiation 102 from the reflected radiation 103 can be achieved without any change in the structure of the system.

Embodiment 2

Figure 8:
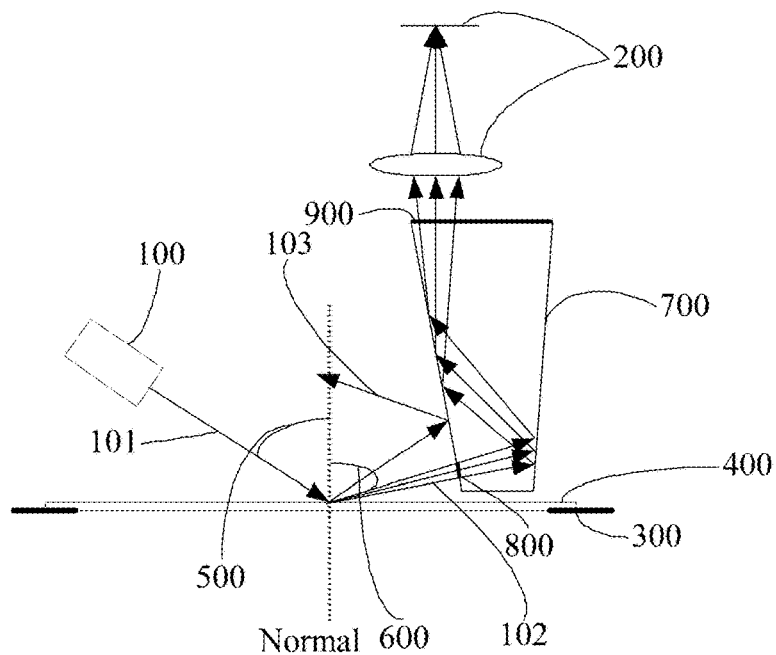
FIG. 8 is a structural schematic of an apparatus for detecting a degree of particulate contamination on a flat panel according to a second embodiment of the present invention.

Referring to FIG. 8 with emphasis, this embodiment differs from Embodiment 1 in that the reflected radiation 103 is externally reflected at the first slanted side S3 (at an area of the first slanted side S3 out of the radiation-transmitting area 800) so that the reflected radiation 103 is not collected by the detector 200.

The reflecting prism is configured in the same way as Embodiment 1.

That is, for alpha1=1, theta1=60° and d1=8 m, from the foregoing equations, we can get:

θ1=60°, θ4=120°, θ2=90°, θ3=90° and l=0.28 mm.

With the reflecting prism configured in such a way, the detector 200 is allowed to always maintain its orientation. In addition, using reflecting prisms of different designs enables a single detector 200 to collection radiation of all angles of scattering 600.

Figure 1:
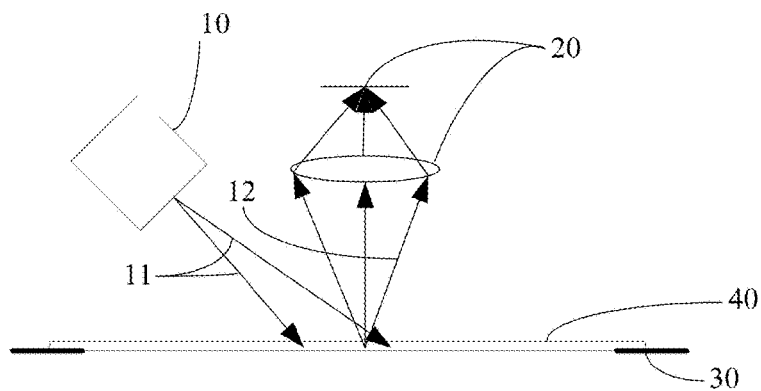
FIG. 1 is a diagram explaining how a conventional apparatus for detecting a degree of particulate contamination on a flat panel works.
Figure 2:
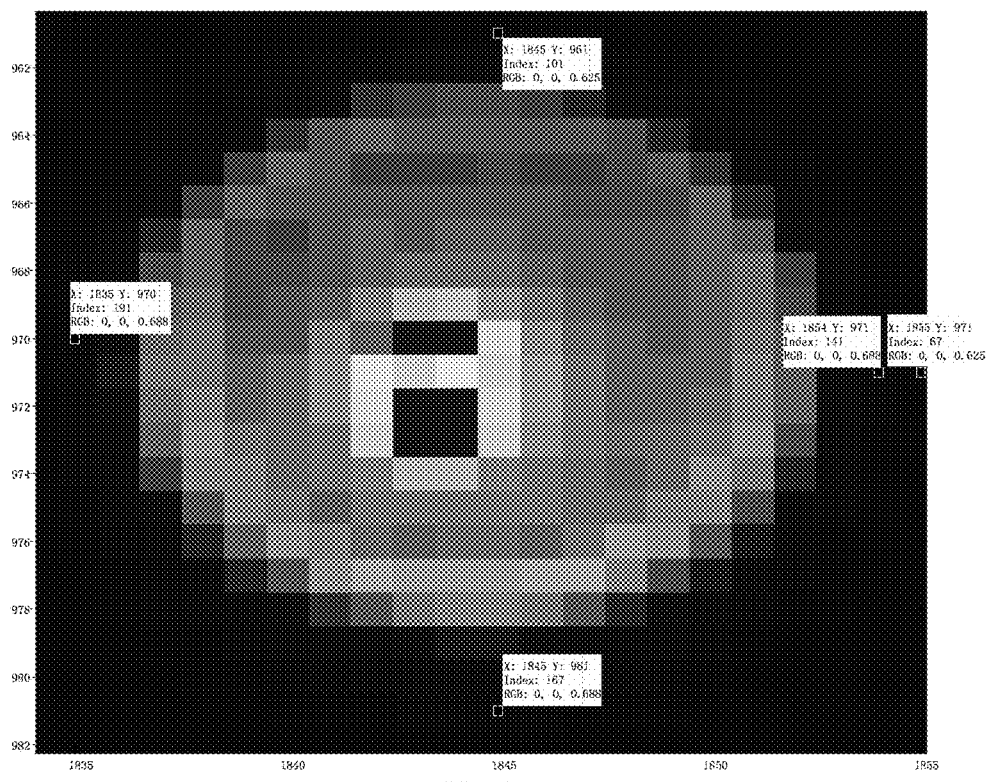
FIGS. 2 and 3 schematically illustrate crosstalk from mirrored particles and crosstalk from a pattern on a bottom surface of a mask, respectively.
Figure 3:
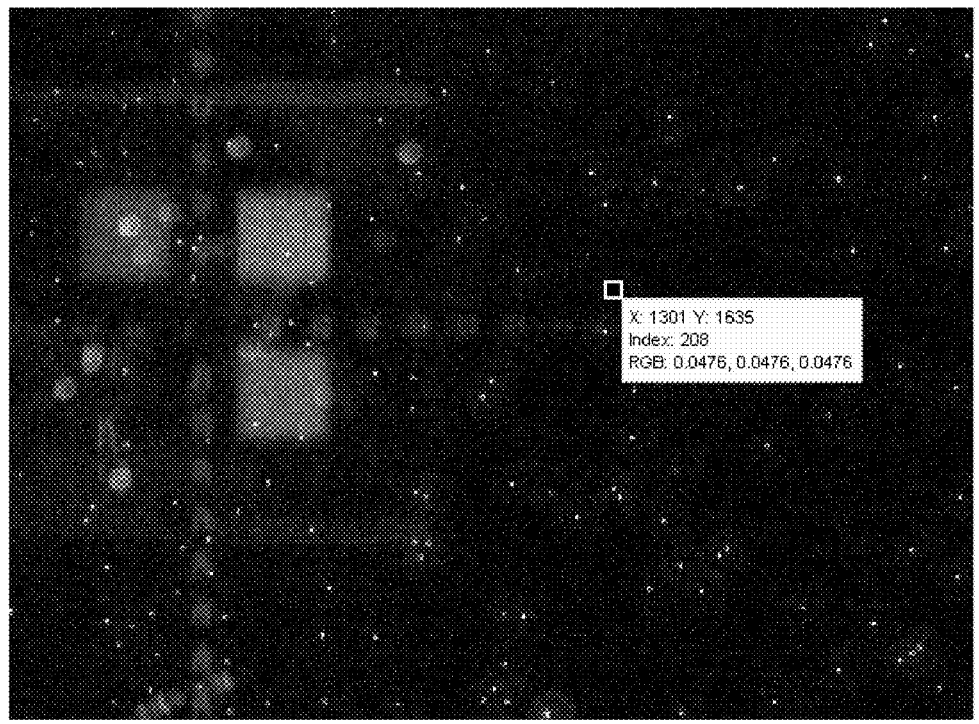
Figure 4:
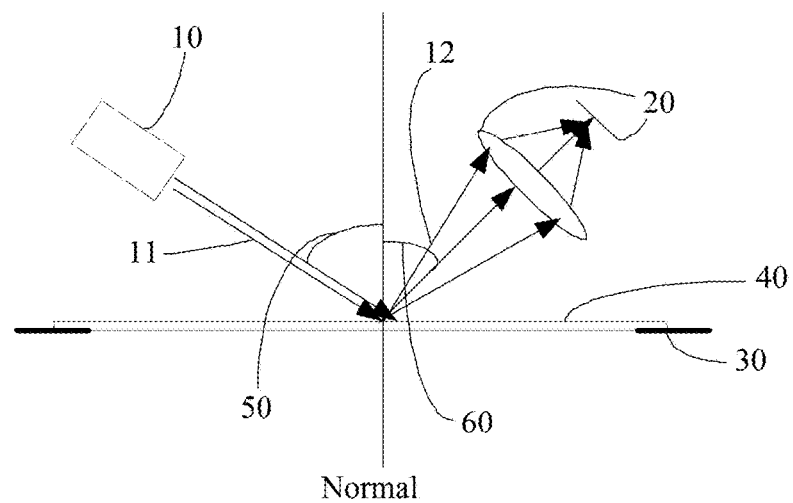
FIG. 4 is a structural schematic of an apparatus for detecting a degree of particulate contamination on a flat panel of the prior art.
Figure 5:
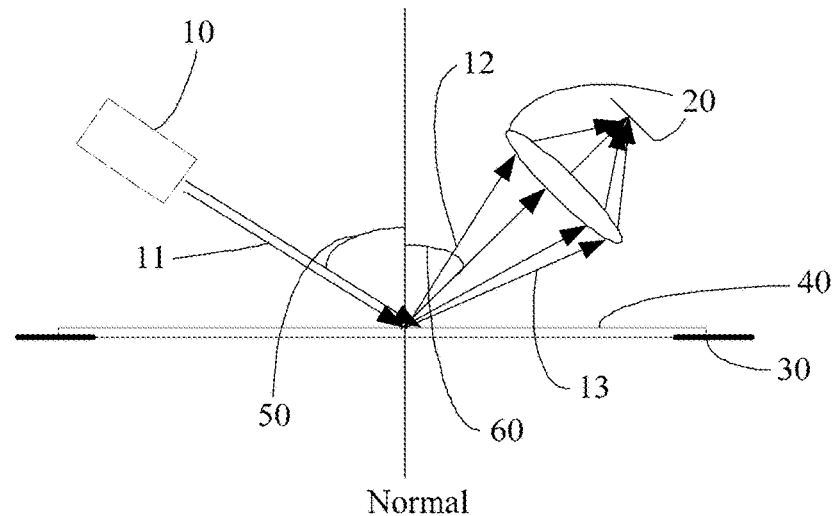
FIG. 5 schematically shows how the apparatus of the prior art is affected by reflected radiation.

Similar to Embodiment 1, the arrangement according to this embodiment can circumvent the issue of partial collection of the reflected radiation reaching an edge of the object-side FoV of the imaging optical path by the detector arising from the scheme as shown in FIG. 4 because the angle between the radiation beam 102 and the reflected radiation 103 is equal to the sum of the angle of scattering 600 and an angular deviation caused by assembly errors, or because the object-side angle of view of the imaging optical path is greater than the angle of scattering 600.

Embodiment 3

Figure 9:
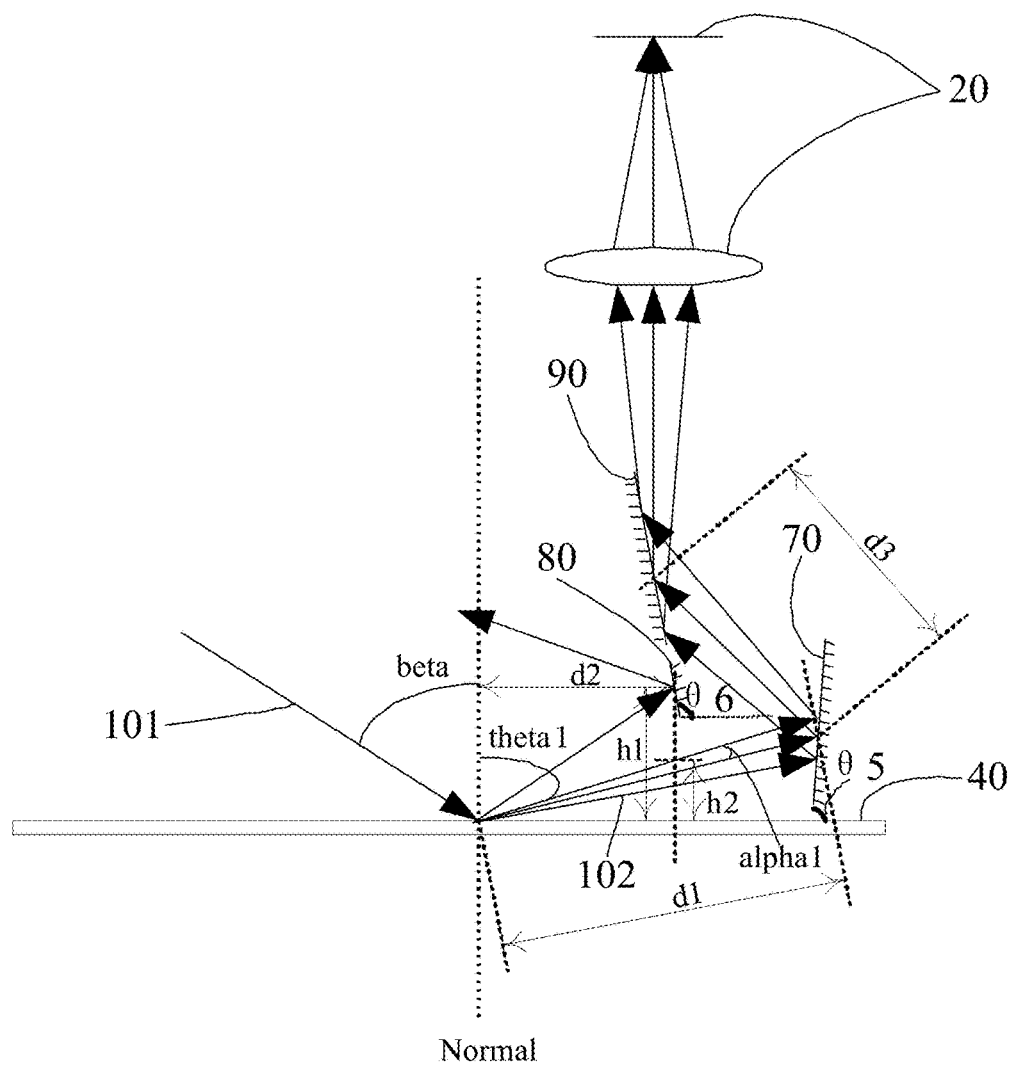
FIG. 9 is a structural schematic of an apparatus for detecting a degree of particulate contamination on a flat panel according to a third embodiment of the present invention.

Referring to FIG. 9 with emphasis, this embodiment differs from Embodiments 1 and 2 in the structure of the beam trimmer. Specifically, in this embodiment, the beam trimmer includes a first reflector 70, a second reflector 90 and a third reflector 80. The scattered radiation 102 is sequentially reflected by the first reflector 70 and the second reflector 90 and is thereby incident on the detector 200. The reflected radiation 103 is reflected by the third reflector 80 so that the reflected radiation 103 is not collected by the detector 200. In other words, in this embodiment, the second reflector 90 and the third reflector 80 together accomplish the function of the first slanted side S3 of the reflecting prism of Embodiment 1 and are oriented at the same angle as the first slanted side S3. Similarly, the first reflector 70 accomplishes the function of the second slanted side S4 of the reflecting prism of Embodiment 1 and is oriented at the same angle as the second slanted side S4.

The first reflector 70, the second reflector 90 and the third reflector 80 are configured in the following manner Assuming the angle of incidence of the illumination radiation as beta, the object-side angle of view of the imaging optical path as alpha1, the angle of scattering as theta1, the distance from the center of the illumination FoV to the first reflector 70 with respect to the object-side angle of view of the imaging optical path as d1, the distance from the center of the illumination FoV to a location of the third reflector 80 stricken by the reflected radiation as d2, and the distance between the first reflector 70 and the third reflector 80 along the direction of propagation of the radiation as d3, then we can get:

θ5=θ2 and θ5=180°−1.5×theta1, where θ5 denotes an angle between the first reflector 70 and the flat panel 40; and θ6=θ4 and θ6=180°−theta1, where θ6 denotes an angle between the second reflector 90 and the third reflector 80.

As the angle of scattering of the scattered radiation is relatively small, an area of the first reflector 70 affected by the scattered radiation is equal to about 2×d1×tan(alpha1). Assuming the affected area is a central area of the first reflector 70, then the size of the first reflector 70 should be greater than 2×d1×tan(alpha1).

An area of the second reflector 90 affected by the scattered radiation is about 2×(d1+d3)×tan(alpha1). Assuming the affected area is a central area of the second reflector 90, then the size of the second reflector 90 should be greater than 2×(d1+d3) ×tan(alpha1).

The distance h1 from the location of the third reflector 80 stricken by the reflected radiation to the flat panel 40 satisfies h1=d2/tan(beta). A line perpendicular to the flat panel 40 passing the location will intersect the scattered radiation 102. Therefore, a maximum distance h2 from the scattered radiation 102 to the flat panel 40 corresponding to the location, i.e., the distance from the highest intersection point between the perpendicular line and the scattered radiation 102 to the flat panel 40, satisfies h2=d2/tan(theta1−alpha1). Because beta<theta1−alpha1, there is h1>h2. The third reflector 80 is disposed such that a bottom end of the third reflector 80 locates at a height greater than h2 and smaller than h1. Assuming the stricken location is a center of the third reflector 80, then the size of third reflector 80 should be greater than zero and smaller than 2×(h1−h2).

The combination of the first, second and third reflector 70, 90, 80 is functionally equivalent to the reflecting prism of Embodiments 1 and 2 and can offer the same benefits. It is a matter of course that other elements or components than those described above may also be used to achieve the same benefits, and such substitutions are considered as equivalents to the foregoing embodiments.

In summary, the present invention provides an apparatus for detecting a degree of particulate contamination on a flat panel, including: an illuminator 100 configured to create an illumination FoV; a detector 200, configured to collect scattered radiation 102 resulting from a radiation beam 101 that is produced by the illuminator 100 and scattered on contaminants on the surface of a flat panel under test 400, the detector 200 having a radiation collection surface perpendicular to a normal to the surface of the flat panel under test 400 on which the radiation beam 101 produced by the illuminator 100 is incident on; and a beam trimmer configured to separate the scattered radiation 102 from reflected radiation 103 resulting from the radiation beam 101 that is reflected by the top surface of the flat panel under test 400. Compared with conventional apparatuses, the present invention adds the beam trimmer between the illuminator 100 and the detector 200 to separate the scattered radiation 102 from the reflected radiation 103 so as to ensure the reflected radiation 103 not to reach the detector 200. In addition, configuring the radiation collection surface of the detector 200 perpendicular to the normal to the surface of the flat panel under test 400 on which the radiation beam 101 produced by the illuminator 100 can improve the adaptability to different system configurations.

It is apparent that those skilled in the art can make various modifications and variations to the present invention without departing from the spirit and scope thereof Accordingly, it is intended that all such modifications and variations are embraced in the scope of the invention if they fall within the scope of the appended claims and or equivalents thereof

What is claimed is:

1. An apparatus for detecting a degree of particulate contamination on a flat panel, comprising:
    an illuminator configured for producing a radiation beam, wherein the radiation beam is scattered by contaminants on a surface of a flat panel under test and results in a scattered radiation, and the radiation beam is reflected by the surface of the flat panel under test and results in a reflected radiation;

a detector configured for collecting the scattered radiation, the detector having a radiation collection surface perpendicular to a normal of the surface of the flat panel under test; and a beam trimmer configured for separating the reflected radiation from the scattered radiation, the beam trimmer comprising a first optical member and a second optical member, the first optical member disposed in correspondence with the scattered radiation and configured for directing the scattered radiation to be collected by the detector, the second optical member disposed in correspondence with the reflected radiation and configured for directing the reflected radiation away from the detector.

2. The apparatus of claim 1, wherein the scattered radiation is directed to be incident at right angles on the radiation collection surface of the detector and is thereby collected by the detector.

3. The apparatus of claim 1, wherein the detector comprises an imaging optical path and a time-delay integration camera, and wherein after being separated from the reflected radiation by the beam trimmer, the scattered radiation is converged onto the time-delay integration camera via the imaging optical path.

4. The apparatus of claim 1, wherein: the first optical member comprises a first reflector and a second reflector; the second optical member comprises a third reflector; the first reflector faces toward the scattered radiation; the scattered radiation is sequentially reflected by the first reflector and the second reflector and is thereby incident on the detector; the third reflector faces toward the reflected radiation; and the reflected radiation is reflected by the third reflector so that the reflected radiation is not collected by the detector.

5. The apparatus of claim 4, wherein: an angle θ5 between the first reflector and the flat panel under test satisfies θ5=180°1.5×theta1; the second reflector is disposed on a same line as the third reflector and is closer to the flat panel under test with respect to the third reflector; the second reflector and the third reflector are both oriented at an angle θ6 with respect to the flat panel under test, which satisfies θ6=180°−theta1; and a lengthwise dimension of the first reflector is greater than 2×d1×tan(alpha1), a lengthwise dimension of the second reflector is greater than 2×(d1+d3)×tan(alpha1) and a lengthwise dimension of the third reflector is greater than 0 and smaller than 2×(h1−h2), where theta1 denotes an angle between the optical axis of the scattered radiation and the normal of the surface of the flat panel under test; alpha1 denotes an object-side angle of view of the scattered radiation with respect to the first reflector; d1 denotes a distance from a center of the illumination field of view created by the illuminator on the surface of the flat panel under test to an optical axis of the second reflector extending along a propagation direction of the scattered radiation; h1 denotes a distance from a location of the third reflector stricken by the reflected radiation to the flat panel under test, which satisfies h1=d2/tan(beta); h2 denotes a distance from a highest intersection point between the scattered radiation and a line that is perpendicular to the flat panel under test and passes the location of the third reflector stricken by the reflected radiation to the flat panel under test, which satisfies h2=d2/tan(theta1/alpha1); and beta denotes an angle between the normal of the surface of the flat panel under test and the radiation beam.

6. The apparatus of claim 5, wherein the illumination field of view created by the illuminator is a linear illumination field of view.

7. The apparatus of claim 1, wherein the beam trimmer comprises a reflecting prism with an outer surface of the reflecting prism defining a first radiation-transmitting area, a second radiation-transmitting area and an outer radiation-reflecting area, the first radiation-transmitting area, the second radiation-transmitting area and an inner radiation-reflecting area of the reflecting prism together constituting the first optical member, the first radiation-transmitting area facing toward the scattered radiation, the second radiation-transmitting area facing toward the detector, the reflecting prism configured for directing the scattered radiation to pass through the first radiation-transmitting area onto the inner radiation-reflecting area and further directed by the inner radiation-reflecting area to pass through the second radiation-transmitting area onto the detector, the outer radiation-reflecting area on the outer surface of the reflecting prism corresponding to the reflected radiation and constituting the second optical member, the reflected radiation being incident on and reflected by the outer radiation-reflecting area so as not to be received by the detector.

8. The apparatus of claim 7, wherein: the reflecting prism has a cross-section in a shape of a trapezoid with a top surface, a bottom surface, a first slanted side and a second slanted side; the top surface and the bottom surface are parallel to the surface of the flat panel under test; the bottom surface is closer to the detector with respect to the top surface; the first slanted side defines the first radiation-transmitting area corresponding to the scattered radiation; the bottom surface defines the second radiation-transmitting area; and the scattered radiation enters the reflecting prism through the first slanted side and is first incident onto and reflected by an inner surface of the second slanted side of the reflecting prism and then incident onto and reflected by an inner surface of the first slanted side so that the scattered radiation exits the reflecting prism through the bottom surface and is finally collected by the detector.

9. The apparatus of claim 8, wherein the first slanted side is perpendicular to an optical axis of the scattered radiation, and when defining an angle between the first slanted side and the bottom surface as a first angle θ1, an angle between the bottom surface and the second slanted side as a second angle θ2, an angle between the second slanted side and the top surface as a third angle θ3 and an angle between the top surface and the first slanted side as a fourth angle θ4, the first to fourth angles, as well as a diameter/of the first radiation-transmitting area on the first slanted side of the reflecting prism, satisfy:

θ1=90°−(90°−theta1);

θ2=180°−1.5×theta1;

θ3=1.5×theta1;

θ4=180°−theta1; and l=2×d1×tan(alpha1)

where, theta1 denotes an angle between the optical axis of the scattered radiation and the normal of the surface of the flat panel under test, alpha1 represents an object-side angle of view of the scattered radiation with respect to the reflecting prism, and d1 denotes a distance from a center of an illumination field of view created by the illuminator on the surface of the flat panel under test to the first slanted side of the reflecting prism.

10. The apparatus of claim 8, wherein the reflecting prism has a cross-section in a shape of a right trapezoid.

11. The apparatus of claim 9, wherein the illumination field of view created by the illuminator is a linear illumination field of view.

\* \* \* \* \*